United States Patent [19]

Stern

[11] Patent Number: 4,783,166

[45] Date of Patent: Nov. 8, 1988

[54] ARRANGEMENT FOR IMPROVING VISUAL DETECTION OF PAINTED AREAS RELATIVE TO SURROUNDING MATERIAL

[75] Inventor: Howard Stern, Greenlawn, N.Y.

[73] Assignee: Robotic Vision Systems, Inc., Hauppauge, N.Y.

[21] Appl. No.: 73,363

[22] Filed: Jul. 15, 1987

[51] Int. Cl.$^4$ .................... G01N 1/00; G01N 21/64; G01N 21/27

[52] U.S. Cl. .................... 356/36; 250/459.1; 356/402; 356/372

[58] Field of Search .................... 356/36, 402, 445, 372, 356/375; 250/458.1, 459.1, 372

[56] References Cited

U.S. PATENT DOCUMENTS

| | | | |
|---|---|---|---|
| 3,577,885 | 5/1971 | Wells | 250/459.1 X |
| 3,617,744 | 11/1971 | Irish | 356/398 |
| 3,641,344 | 2/1972 | Markle | 250/458.1 X |
| 3,713,741 | 1/1973 | Sheehan, III. | 356/416 X |
| 3,748,469 | 7/1973 | Molina | 250/459.1 |
| 3,904,293 | 9/1975 | Gee | 356/448 X |
| 3,965,360 | 6/1976 | Sakasegawa et al. | 250/372 X |
| 3,973,129 | 8/1976 | Blumberg et al. | 250/461.2 |
| 3,994,586 | 11/1976 | Sharkins et al. | 356/445 X |
| 4,140,397 | 2/1979 | Gara | 356/448 X |
| 4,152,723 | 5/1979 | McMahon et al. | 250/458.1 X |
| 4,199,219 | 4/1980 | Suzki et al. | 356/445 X |
| 4,258,264 | 3/1981 | Kotera et al. | 250/459.1 X |
| 4,281,342 | 7/1981 | Veda et al. | 356/426 X |
| 4,337,566 | 7/1982 | DiMatteo et al. | 51/326 X |
| 4,348,803 | 9/1982 | Sasaki | 356/402 X |
| 4,355,447 | 10/1982 | Di Matteo et al. | 364/474 X |
| 4,393,311 | 7/1983 | Feldman et al. | 250/459.1 |

FOREIGN PATENT DOCUMENTS 52-20890  2/1977  Japan .................... 356/416

Primary Examiner—Vincent P. McGraw
Attorney, Agent, or Firm—Max Fogiel

[57] ABSTRACT

Two embodiments for enhancing the detection of a selected area on a surface that may produce specular reflection. In the first embodiment the selected area is coated with a material which will only reflect incident radiation over a narrow band of frequencies and the surface is irradiated with a broadband radiation source that includes the reflectance band of the coating. The irradiated surface is imaged on an imaging device such as a TV camera through a filter selected to reject all but the narrow band of frequencies reflected from the selected area. Further enhancement is provided by comparing the results with those from the same signals filtered by a filter that is the complement of the first. Standard signal processing can then be applied. The second embodiment involves coating the selected surface area with a material possessing the property of radiating energy at one frequency when irradiated by energy at another frequency; irradiating the surface with energy at that other frequency; and viewing the surface with a TV camera through a filter that passes the reradiated energy but blocks the irradiation energy. Complementary filtering could also be applied for further enhancement. Standard signal processing can then be applied to automatically identify the selected area.

14 Claims, 4 Drawing Sheets (a)

(b)

FIG. 4
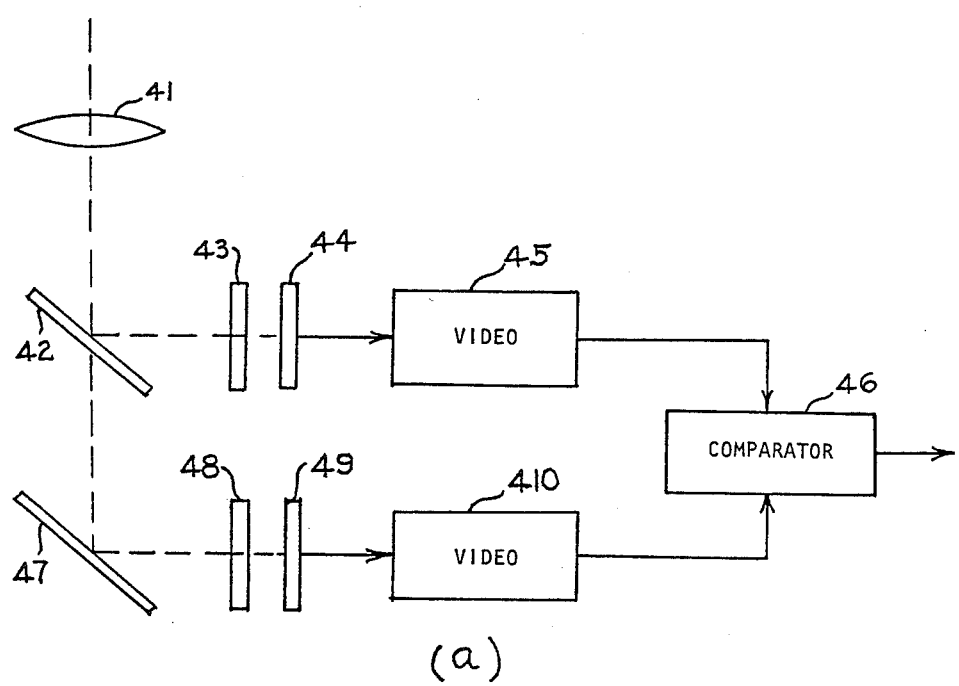
(a)
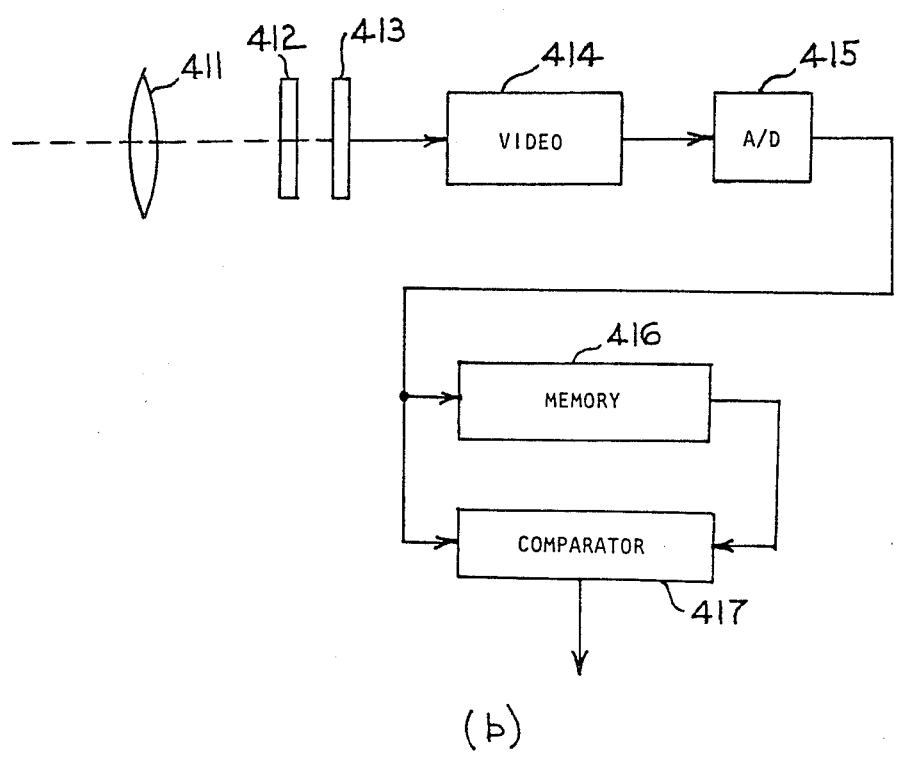
(b)

1

ARRANGEMENT FOR IMPROVING VISUAL DETECTION OF PAINTED AREAS RELATIVE TO SURROUNDING MATERIAL

BACKGROUND OF THE INVENTION

In the application of robotics, it is sometimes necessary to distinguish a painted portion of a surface from a surrounding surface that may be quite smooth, giving rise to specular reflection of incident light. In particular, in applying the methods of U.S. Pat. Nos. 4,337,566 and 4,355,447 in which holes or grooves are cut into a surface, painted, and the diameter visually monitored in a feedback loop controlling the machining of the surface, the specular reflection of the newly machined surface can make the painted surface indistinguishable.

The present invention provides an arrangement to enhance the visual detection of the painted areas relative to the surrounding material.

SUMMARY OF THE INVENTION

It is an object of the present invention to overcome the aforementioned prior-art disadvantages.

More particularly, it is an object of the present invention to avoid the deleterious effects of specular reflections when using optical means to identify a surface area surrounded by a specularly reflective surface such as when applying U.S. Pat. Nos. 4,337,566 or 4,355,447.

In keeping with this object and with still others which will become apparent as the description proceeds, one aspect of the invention resides in using white or broadband light projection and narrow-band paint with complementary filtering of the reflected light. Another aspect of the invention resides in using a paint that radiates energy at one frequency when excited by incident energy of another frequency.

Where broad-band light is reflected from a diffuse surface area with maximum reflectance over a narrow band of frequencies within the incident band, and that surface area is surrounded by a surface with broad-band reflectance, it is possible to enhance the detection of the first mentioned surface by passing the reflected light through a narrow-band filter. The enhancement can be made greater by using complementary filters and subtracting or comparing the outputs.

An alternate method is obtained when the surface area of interest is coated with a substance that possesses the property of radiating energy at a frequency different from that of the incident energy. The surrounding area, possessing normal reflective properties, will reflect the incident energy which can then be blocked by a filter that excludes that frequency range but passes the energy reradiated from the area of interest. Complementary filtering can also be employed for further enhancement. Two-dimensional and three-dimensional measurements can also be made possible in the presence of specular surfaces by using this method of surface enhancement.

The novel features which are considered as characteristic for the invention are set forth in particular in the appended claims. The invention itself, however, both as to its construction and its method of operation, together with additional objects and advantages thereof will be best understood from the following description of specific embodiments when read in connection with the accompanying drawings.

BRIEF DESCRIPTION OF THE DRAWINGS

FIG. 4 is a schematic view showing the parallel and serial implementations of imaging the scene and processing the video signals generated by the scene.

DESCRIPTION OF THE PREFERRED EMBODIMENTS

Figure 1:
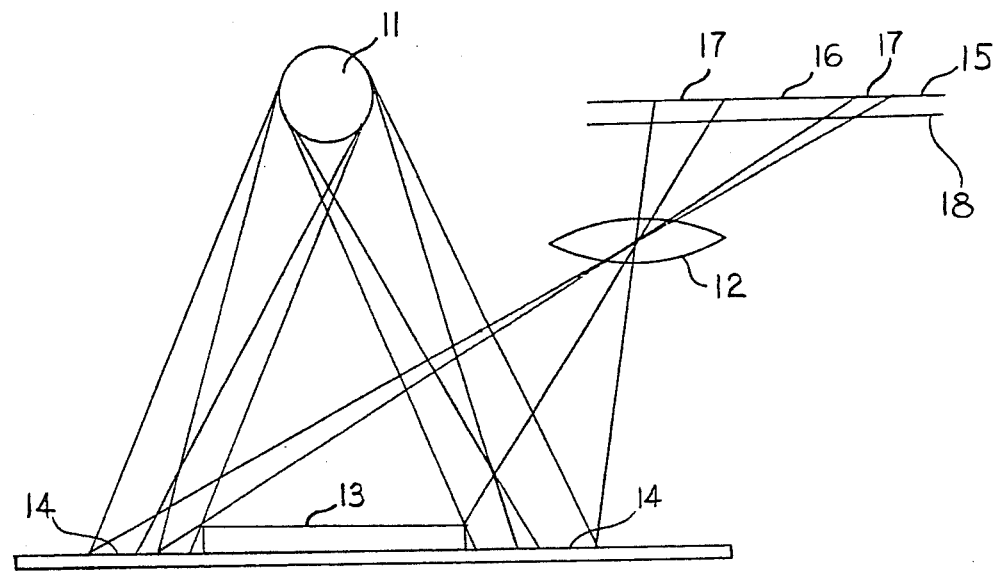
FIG. 1 is a schematic view and shows a cross section of an illuminated surface imaged onto a light sensitive surface.
Figure 2:
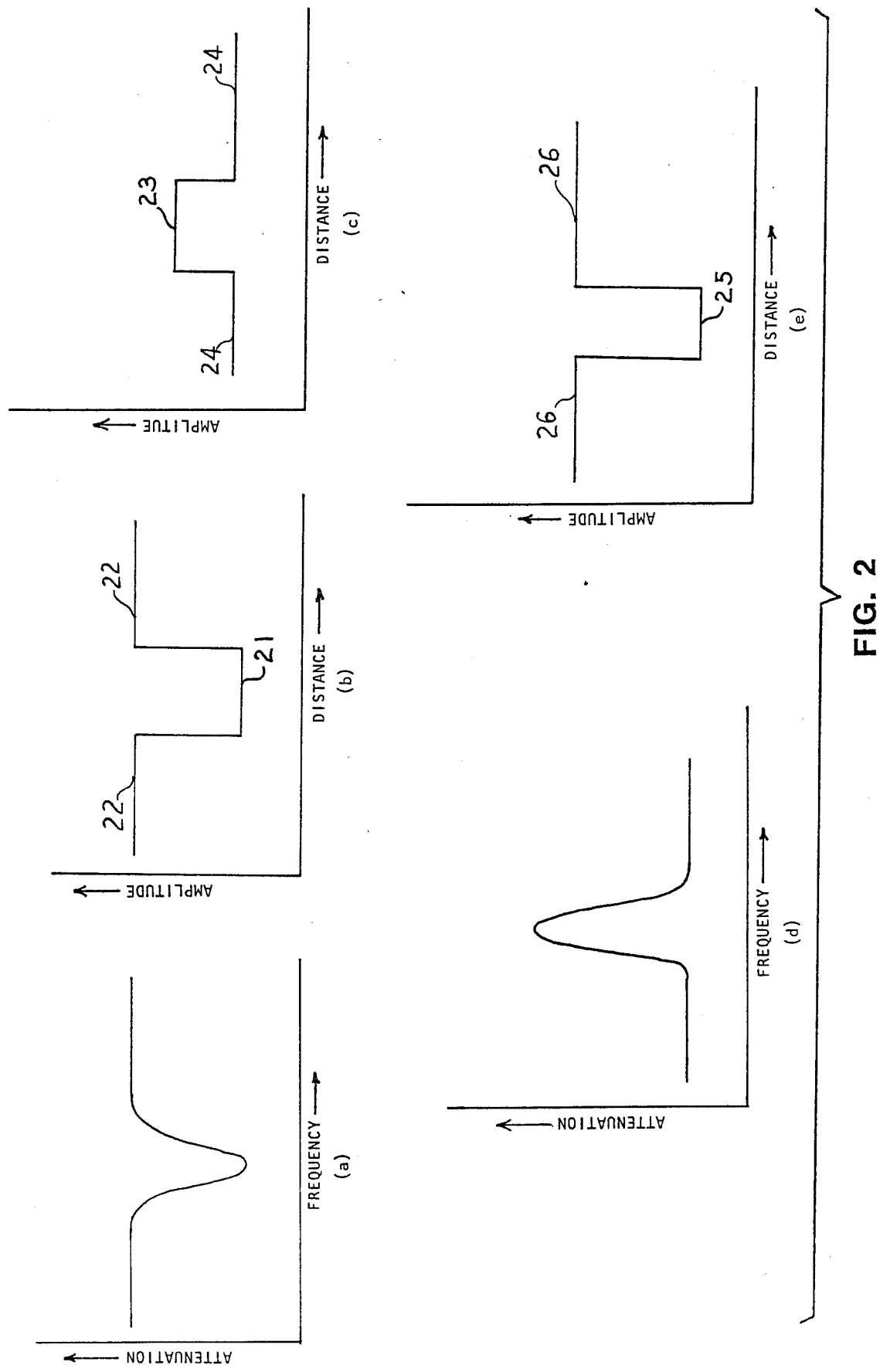
FIG. 2a-e shows graphical presentations of filter selectivity curves and light intensity profiles before and after filtering.

FIG. 1 illustrates a situation in which a broad-band illumination source 11 is specularly reflected by surface areas 14 and imaged by lens 12 on to a light sensitive surface 15 at areas 17. Source 11 also illuminates surface 13 which reflects (preferably diffusely) the light. The reflected light is imaged by lens 12 onto surface 15 at area 16. FIG. 2b represents graphically the amplitude of the reflected energy in the directon of lens 12 from surfaces 13 and 14. Surfaces 14 are shown by level 22 to reflect much more energy than level 21 of surface 13. Although level 22 is shown as uniformly greater than level 21 for simplicity, in reality many dips in the level will be present so that no distinguishing characteristics will be present to reliably enable automatic detection of the desired area 13.

By applying a narrow-band diffuse reflective coating (a specular coating could be used in applications where the relative positions of the source, surface and optical receiver are controlled for sufficient reflection) to the desired area 13 and interposing a matching narrow-band filter 18 that passes, with low attenuation, only the energy in a narrow frequency range surrounding the peak reflectance frequency of the coating as shown in graph 2a, the energy profile incident on surface 15 will be changed from the unfiltered profile 2b to the filtered profile 2c. For applications in which the surrounding area 14 is not very specular, this may be sufficient to provide a level 23 for the desired area image that is greater than the level 24 of the surrounding area image. This could provide a means of automatically determining which part of the image on surface 15 belonged to the desired area circuit 13. However, this would not be reliable in applications of high specular response, since the energy of the source at the center frequency of the filter could be nearly 100 percent reflected and the desired area image would have a lower energy level than the specular response image on surface 15. This would lead to a false determination by the automatic detection equipment. To resolve this problem, the present invention employs a second filter 18 having a complementary attenuation function of the first filter whose characteristic is shown in 2d. As long as the illumination source is broader than the major filter response and the response of the reflectance of the desired area, the filtered energy profile 2e of energy profile 2b will provide levels 26 in surrounding areas 17 greater than levels 24, and level 25 less than level 23 in the desired area 16 on surface 15. Now by comparison, the desired area can be automatically identified by an equipment that compares the two energy profiles such as shown in FIG. 4. The comparison may take place simultaneously as in 4a or, if the scene is relatively unchanged between measurement times, sequentially as in 4b. In 4a, the reflected light collected by lens 41 is focussed on surfaces 44 and 49 via beam splitter 42 and reflector 47, and complementary filters 43 and 48. Light sensitive surfaces 44 and 49 might be TV sensor chips which are interfaced to comparator 46 via video amplifiers 45 and 410. Such processing is well known in the state of the art in image processing. The essential element for reliable area identification is providing a reliable criterion such as is provided by the complementary filters 43 and 48 forcing the desired area response from one to exceed the other with the reverse being true elsewhere.

In FIG. 4b, the light collected by lens 411 is imaged on surface 413 after being filtered by filter 412. Surface 413 may be a TV sensor chip interfaced to an A/D converter 415 by a video amplifier 414. Memory 416 stores the measured digital data of the scene produced by A/D converter 415. Filter 412 is exchanged for a complementary filter, exhibiting substantially the reverse attenuation characteristic of the first filter; the exchange is made mechanically or electrically. The new output of A/D converter 415 is compared point-by-point by comparator 417 against corresponding memorized values from memory 416. Where the output of the filter having low attenuation in the frequency band of the reflective coating on the desired area exceeds that of the complementary filter, the point examined is declared to be within the desired area. All other points are declared external to the desired area.

Figure 3:
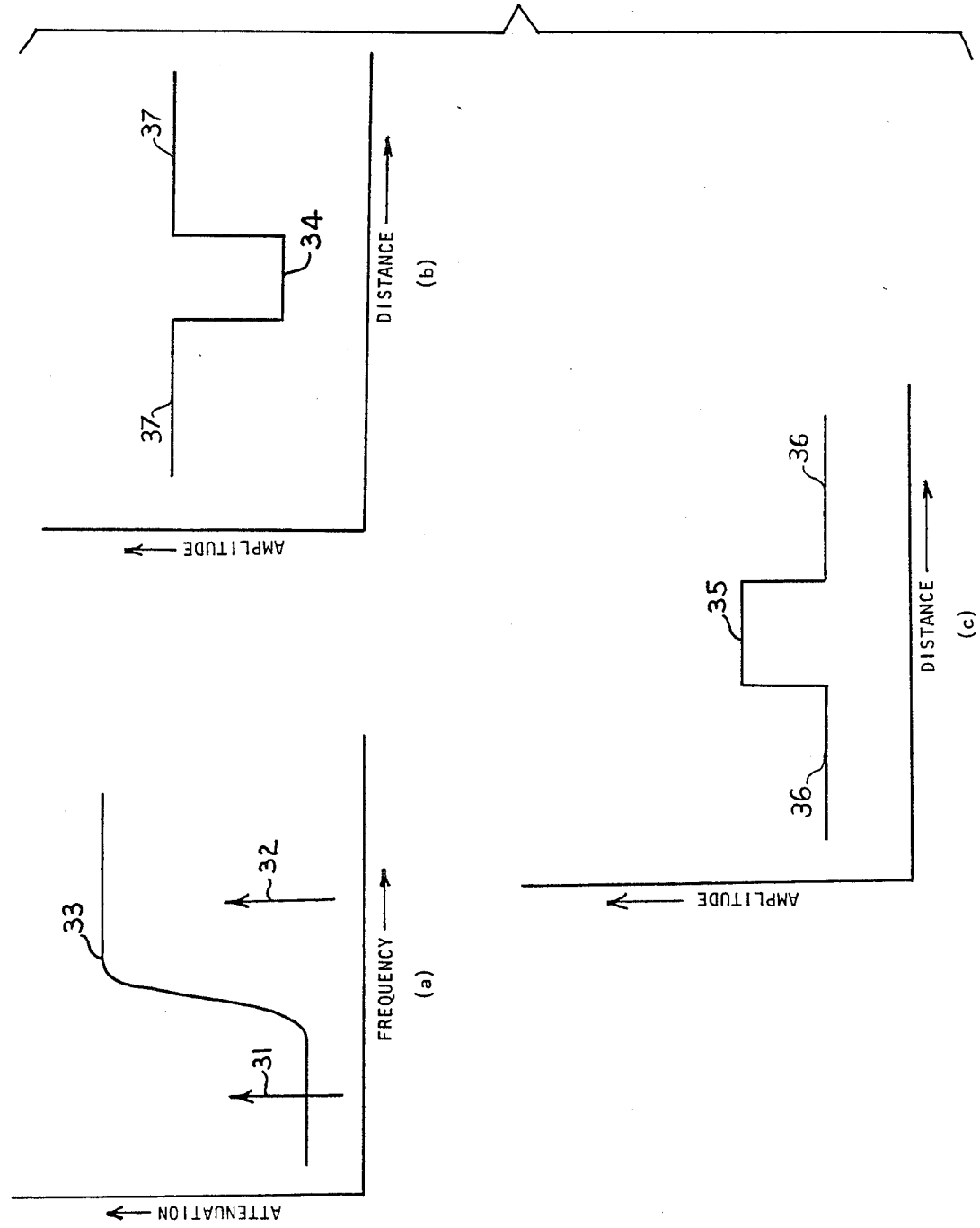
FIG. 3 illustrates graphically a filter characteristic and light intensity profiles for a system with a surface coating that reradiates energy at a frequency different from the incident energy.

A second preferred embodiment of the invention can also be envisioned from FIG. 1. Now, however, the area 13 desired to be automatically identified, must be coated with a material that radiates energy when irradiated. It is preferrable that the energy radiated by the coating be narrow band to allow greater discrimination against other radiation by filtering. As illustrated in FIG. 3a, it is necessary that the radiation 31 from the coating be induced via radiation 32 from a part of the spectrum that is different from that of the coating radiation 31. This will allow narrow band filtering with a characteristic frequency response as in FIG. 2a where the frequencies of low attenuation coincide with the reradiated energy 31; or low (or high for reversed frequencies) pass filtering 33, as shown in FIG. 3a. FIG. 3b shows how the energy profile might appear without filtering on detection surface 15 where energy reradiated from the desired area 13 is imaged at 16 and produces level 34 and the surrounding area 14 image to areas 17 with levels 37 that may be greater or less than level 34. After filtering, the energy profile will be given in FIG. 3c where the desired image area 16 energy level 34 is slightly attenuated to level 35 and the surrounding energy levels 37 are greatly attenuated to levels 36. Because of the wide separation of frequencies 31 and 32 that are possible in this embodiment (incident radiation 32 may be ultra violet and reradiation 31 may be visible or infrared), filter attenuation should be adequate to separate the desired image from the surrounding images. If necessary, complementary filtering, as described in the first embodiment, could be employed.

Figure 5:
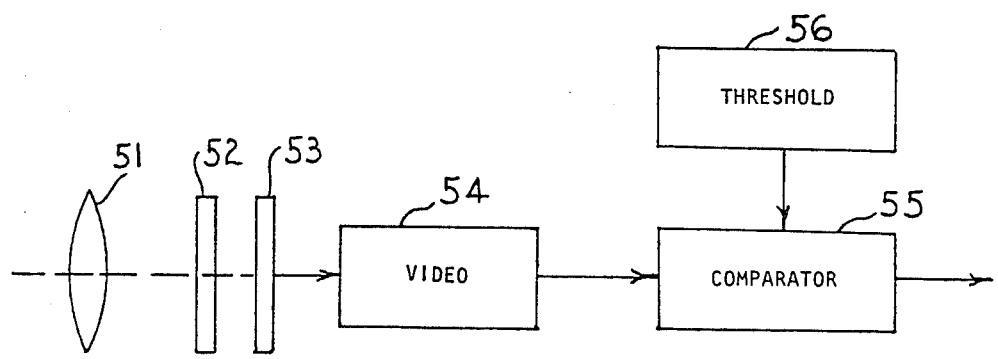
FIG. 5 is a schematic view showing the processing for another embodiment.

The automatic detection processing for the second embodiment can be simpler than for the first embodiment as shown in FIG. 5. Lens 51 images the scene on surface 53 through filter 52. Surface 53 may be a TV sensor chip which supplies a video signal proportional to the energy in the various parts of the image. Amplifier 54 amplifies the signal and applies the amplified signal to one input of comparator 55. The video signal represents energy level versus position as voltage versus time so that the comparator 55 produces an automatic indication of the location of the desired surface area as a signal versus time. The comparator 55 does this by producing a distinctive signal (e.g. a high level) when the amplified signal is greater than its other input signal supplied by threshold circuit 56, and a different signal (e.g. a low signal) when the amplified signal is less than the threshold signal.

More sophisticated processing can then be performed on the comparator 55 output signal for final area identification. For example, more reliable identification may be obtained by comparing the results of the comparator output with apriori knowledge of the desired area size and shape. Comparator reports that do not pass such a reasonableness test may be discarded. The threshold circuit 56 may also adapt its output signal to changing scene conditions. For example, the threshold may be made equal to a fraction of the largest signal or a multiple of the overall noise level. These techniques are well-known in the field of image processing.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed is:

1. A method for improving detectability of a predetermined area on a surface surrounded by surfaces that may contain specular reflecting regions, comprising the steps of: coating a predetermined area on a surface with material radiating energy in a frequency band other that that of a radiation source when irradiated by said source; irradiating said surface with said radiation source; imaging a first predetermined portion of reflected and reradiated energy from said surface onto an image detection surface after passing through a first filter having low attenuation in a frequency band of radiation from said predetermined area coating and high attenuation at least in the frequency band of said radiation source; imaging a second predetermined portion of reflected and reradiated energy from said surface onto an image detection surface after passing through a second filter having low attenuation for all frequencies except those of the radiation band of the coating; subtracting the second detected image from the first detected image and forming a difference image; and automatically detecting said predetermined surface area by said difference image; said two filters being in operation at the same frequency whereby one filter is a band pass filter and the other filter is a band reject filter, so that uncertainty is prevented due to unknown selectivity of reflectance of surfaces as wavelength is changed, said predetermined surface area being detected independent of any absorption band present in said radiation source.

2. A method as defined in claim 1, and imaging the two filtered images onto separate image detection surfaces and comparing the outputs for automatically detecting said predetermined surface area.

3. A method as defined in claim 1, and imaging the first filtered image on an image detection surface; storing the data related to signal strength; changing the filter characteristic to provide the other attenuation function; imaging the second filtered image on the image detection surface; and comparing the data related to signal strength with the stored data for automatically detecting said predetermined surface area.

4. A method as defined in claim 2, and indicating said predetermined surface to be present only where the signal derived from the first detected image represents a greater energy level than the signal derived from the second detected image.

5. A method as defined in claim 3, and indicating said predetermined surface to be present only where the signal derived from the first detected image represents a greater energy level than the signal derived from the second detected image.

6. A method for automatic identification of said predetermined area on a surface, according to the steps of claim 4, and comparing said detected predetermined surface area with predetermined characteristics of the measured scene to improve reliability of identification.

7. A method for automatic identification of said predetermined area on a surface according to the steps of claim 5, and comparing said detected predetermined surface area with predetermined characteristics of the measured scene to improve reliability of identification.

8. A method for automatically detecting energy reflected from a predetermined area on a surface comprising the steps of: coating said predetermined area with a material having selective wavelength reflection characteristics, said material reflecting a narrow band of energy within a broadband radiation source, said narrow band forming a principal reflectance band; irradiating said surface with a broadband radiation source; imaging a portion of the reflected energy from said surface onto a first image detection surface after passing through a narrow bandpass filter having low attenuation at frequencies substantially encompassing said principal reflectance band of the coating, producing a first detected filtered image; imaging a portion of said reflected energy from said surface onto a second image detection surface after passing through a band reject filter having low attenuation for all frequencies except those of the principal reflectance band of the coating, producing a second detected filtered image; and comparing the detected outputs for automatically detecting said predetermined surface area.

9. A method as defined in claim 8, and indicating said predetermined surface to be present only where the signal derived from the path with said narrow-band filter represents a greater reflected energy than a signal derived from the path with said complementary band-reject filter.

10. A method for automatic identification of said predetermined area on a surface, according to the steps of claim 9, and comparing said detected predetermined surface area with predetermined characteristics of the measured scene to improve reliability of the identification.

11. A method for automatically detecting energy reflected from a predetermined area on a surface comprising the steps of: coating said predetermined area with a material having selective wavelength reflection characteristics, said material reflecting a narrow band of energy within a broadband radiation source, said narrow band forming a principal reflectance band; irradiating said surface with a broadband radiation source; imaging a portion of the reflected energy from said surface onto a suitable image detection surface after passing through a narrow bandpass filter having low attenuation at frequencies substantially encompassing said principal reflectance band of the coating, producing a first detected filtered image; storing the data related to signal strength; imaging all reflected energy from said surface onto said image detection surface after passing through a band reject filter having low attenuation for all frequencies except those of the principal reflectance band of the coating, producing a second detected filtered image; and comparing the data related to signal strength with said stored data for automatically detecting said predetermined surface area.

12. A method for improving the image contrast between the detected energy reflected from a predetermined area on a surface and the surrounding reflecting areas including specular reflecting areas, comprising the steps of: coating said predetermined area with a material having selective wavelength reflection characteristics, said material reflecting a narrow band of energy within a broadband radiation source, said narrow band forming a principal reflectance band; irradiating said surface with a broadband radiation source; imaging a portion of the reflected energy from said surface onto a first image detection surface after passing through a narrow bandpass filter having low attenuation at frequencies substantially encompassing said principal reflectance band of the coating, producing a first detected filtered image; and imaging at least a portion of the said reflected energy onto a suitable image detection surface after passing through a band-reject filter having low attenuation for all frequencies except those of the principal reflectance band of the coating, producing a second detected filtered image.

13. A method for automatically detecting energy reflected from a predetermined area on a surface comprising the steps of: coating said predetermined area with a material having selective wavelength reflection characteristics, said material reflecting a narrow band of energy within a broadband radiation source, said narrow band forming a principal reflectance band; irradiating said surface with a broadband radiation source; imaging all reflected energy from said surface onto a suitable image detection surface after passing through a narrow bandpass filter having low attenuation at frequencies substantially encompassing said principal reflectance band of the coating, producing a first detected filtered image; storing the data related to signal strength; imaging all reflected energy from said surface onto said image detection surface after passing through a band reject filter having a low attenuation for all frequencies except those of the principal reflectance band of the coating, producing a second detected filtered image; comparing the data related to signal strength with said stored data for automatically detecting said predetermined surface area; and indicating said predetermined surface to be present only where the signal derived from the energy filtered by the band pass filter is greater than the signal derived from the energy filtered by the band reject filter.

14. A method for automatic identification of said predetermined area on a surface according to the steps of claim 13, and using said predetermined area characteristics to improve reliability of identification.

* * * * *

UNITED STATES PATENT AND TRADEMARK OFFICE
CERTIFICATE OF CORRECTION

PATENT NO. : 4,783,166

DATED : November 8, 1988

INVENTOR(S) : Howard Stern

It is certified that error appears in the above-identified patent and that said Letters Patent is hereby corrected as shown below:

Claim 1, line 5 (column 4, line 41): change "that" to --than--.

Claim 1, line 22 (column 4, line 58): change ";" to --,--.

Claim 9, line 5: (column 5, line 54): delete "complementary".

Front Page, left column: insert --Related U.S. Application Data
[63] Continuation of Ser. No. 539,726, Oct. 6, 1983, abandoned.--

Signed and Sealed this

Fourth Day of June, 1991

Attest:

HARRY F. MANBECK, JR.

Attesting Officer

Commissioner of Patents and Trademarks